United States Patent
Popovic et al.

(10) Patent No.: US 11,452,464 B2
(45) Date of Patent: Sep. 27, 2022

(54) GUIDANCE TOOLS TO MANUALLY STEER ENDOSCOPE USING PRE-OPERATIVE AND INTRA-OPERATIVE 3D IMAGES

(71) Applicant: KONINKLIJKE PHILIPS N.V., Eindhoven (NL)

(72) Inventors: Aleksandra Popovic, New York, NY (US); Haytham Elhawary, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1036 days.

(21) Appl. No.: 14/394,611

(22) PCT Filed: Apr. 8, 2013

(86) PCT No.: PCT/IB2013/052797
§ 371 (c)(1),
(2) Date: Oct. 15, 2014

(87) PCT Pub. No.: WO2013/156893
PCT Pub. Date: Oct. 24, 2013

(65) Prior Publication Data
US 2015/0073265 A1    Mar. 12, 2015

Related U.S. Application Data

(60) Provisional application No. 61/635,327, filed on Apr. 19, 2012.

(51) Int. Cl.
*A61B 5/06* (2006.01)
*A61B 1/00* (2006.01)
(Continued)

(52) U.S. Cl.
CPC ............ *A61B 5/066* (2013.01); *A61B 1/0005* (2013.01); *A61B 1/00009* (2013.01); *A61B 1/0016* (2013.01); *A61B 1/00045* (2013.01); *A61B 1/04* (2013.01); *A61B 34/20* (2016.02); *A61B 34/25* (2016.02); *A61B 2034/107* (2016.02); *A61B 2090/364* (2016.02); *A61B 2090/365* (2016.02)

(58) Field of Classification Search
CPC combination set(s) only.
See application file for complete search history.

(56) References Cited

U.S. PATENT DOCUMENTS

| 6,332,089 B1 * | 12/2001 | Acker ............... A61B 5/0422 128/899 |
| 2002/0007123 A1 | 1/2002 | Balas |

(Continued)

FOREIGN PATENT DOCUMENTS

| WO | 2010111090 A1 | 9/2010 | |
| WO | WO 2010111090 A1 * | 9/2010 | ......... A61B 1/00039 |

*Primary Examiner* — Luther Behringer

(57) ABSTRACT

Systems and methods for guided endoscope navigation include a registration module (118) configured to, using a processor, register a first set of images (112) with a second set of images (114) of an endoscope (102). A selection module (120) is configured to receive selected areas of interest on the first set of images and transform the selected areas of interest to an endoscope coordinate frame. A guidance module (122) is configured to overlay guidance tools onto the second set of images to permit a user of the endoscope to navigate to the selected areas of interest.

26 Claims, 4 Drawing Sheets

(51) Int. Cl.
  *A61B 34/20* (2016.01)
  *A61B 1/04* (2006.01)
  *A61B 34/00* (2016.01)
  *A61B 90/00* (2016.01)
  *A61B 34/10* (2016.01)

(56) References Cited

U.S. PATENT DOCUMENTS

| | | |
|---|---|---|
| 2002/0049375 A1* | 4/2002 | Strommer ............ A61B 5/0066 600/407 |
| 2002/0077544 A1 | 6/2002 | Shahidi |
| 2006/0004286 A1 | 1/2006 | Chang et al. |
| 2006/0036162 A1 | 2/2006 | Shahidi et al. |
| 2008/0262297 A1 | 10/2008 | Gilboa et al. |
| 2008/0287783 A1 | 11/2008 | Anderson |

\* cited by examiner

GUIDANCE TOOLS TO MANUALLY STEER ENDOSCOPE USING PRE-OPERATIVE AND INTRA-OPERATIVE 3D IMAGES

This disclosure relates to medical instruments and more particularly to guidance tools for manually steering endoscopes.

Coronary artery bypass grafting (CABG) is a surgical procedure for the revascularization of obstructed coronary arteries. Minimally invasive CABG is performed using an endoscope as the only feedback from the operating site. In a standard setup for a minimally invasive CABG procedure, a surgeon uses both hands to hold instruments while an assistant holds the endoscope. The endoscope is typically inserted into the chest cavity from the right side of the patient or from the posterior-anterior direction. This may result in three relevant coordinate systems: the coordinate system of the endoscope (e.g., camera), the coordinate system of the surgeon, and the coordinate system of the assistant. This can lead to a number of problems. For instance, while the surgeon is looking forward at the screen, the camera is representing the anatomy from a side view. In addition, if the camera located on the top of the endoscope were to be rotated 180°, the image would appear inverted on the screen. However, there is currently no way of knowing the camera's orientation. Moreover, the assistant has to respond to instructions from the surgeon as to how to move the endoscope. An order such as "right" may correspond to moving the endoscope left and down, which may be highly counter-intuitive for the assistant and may lead to a trial and error approach. These problems may lead to prolonged operating room time and inefficiencies in the workflow.

In accordance with the present principles, novel solutions for guidance tools for manually steering an endoscope are provided. In one embodiment, the present principles may include registering preoperative and/or intraoperative images with images of an endoscope. Visual cues may be overlaid onto the endoscope view as guidance tools to permit a user to navigate the endoscope towards selected areas of interest. The motion of the endoscope may be tracked in real-time using image features to update the visual cues. In another embodiment, the present principles may pre-orient a camera of an endoscope such that the coordinate system of the camera corresponds with a preferred coordinate system of the user. The camera of the endoscope may be mounted on an actuated platform, which pre-orients the endoscope by rotating the camera to correspond to a preferred direction of the user. Advantageously, the present principles provide for efficient steering to manually navigate an endoscope. This may lead to reduced operating room time and a more efficient workflow.

A system for guided endoscope navigation includes a registration module configured to, using a processor, register a first set of images with a second set of images of an endoscope. A selection module is configured to receive selected areas of interest on the first set of images and transform the selected areas of interest to an endoscope coordinate frame. A guidance module is configured to overlay guidance tools onto the second set of images to permit a user of the endoscope to navigate to the selected areas of interest.

A system for guided endoscope navigation includes a registration module configured to, using a processor, register a first set of images with a second set of images of an endoscope. A selection module is configured to receive selected areas of interest on the first set of images and transform the selected areas of interest to an endoscope coordinate frame. A guidance module is configured to overlay guidance tools onto the second set of images. An actuation module is configured to orient a camera of the endoscope such that a coordinate system of the camera corresponds with a coordinate system of the user to permit a user of the endoscope to navigate to the selected areas of interest.

A method for guided endoscope navigation includes registering, using a processor, a first set of images with a second set of images of an endoscope. Areas of interest are selected on the first set of images and the selected areas of interest are transformed to an endoscope coordinate frame. Guidance tools are overlaid onto the second set of images to permit a user of the endoscope to navigate to the selected areas of interest.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
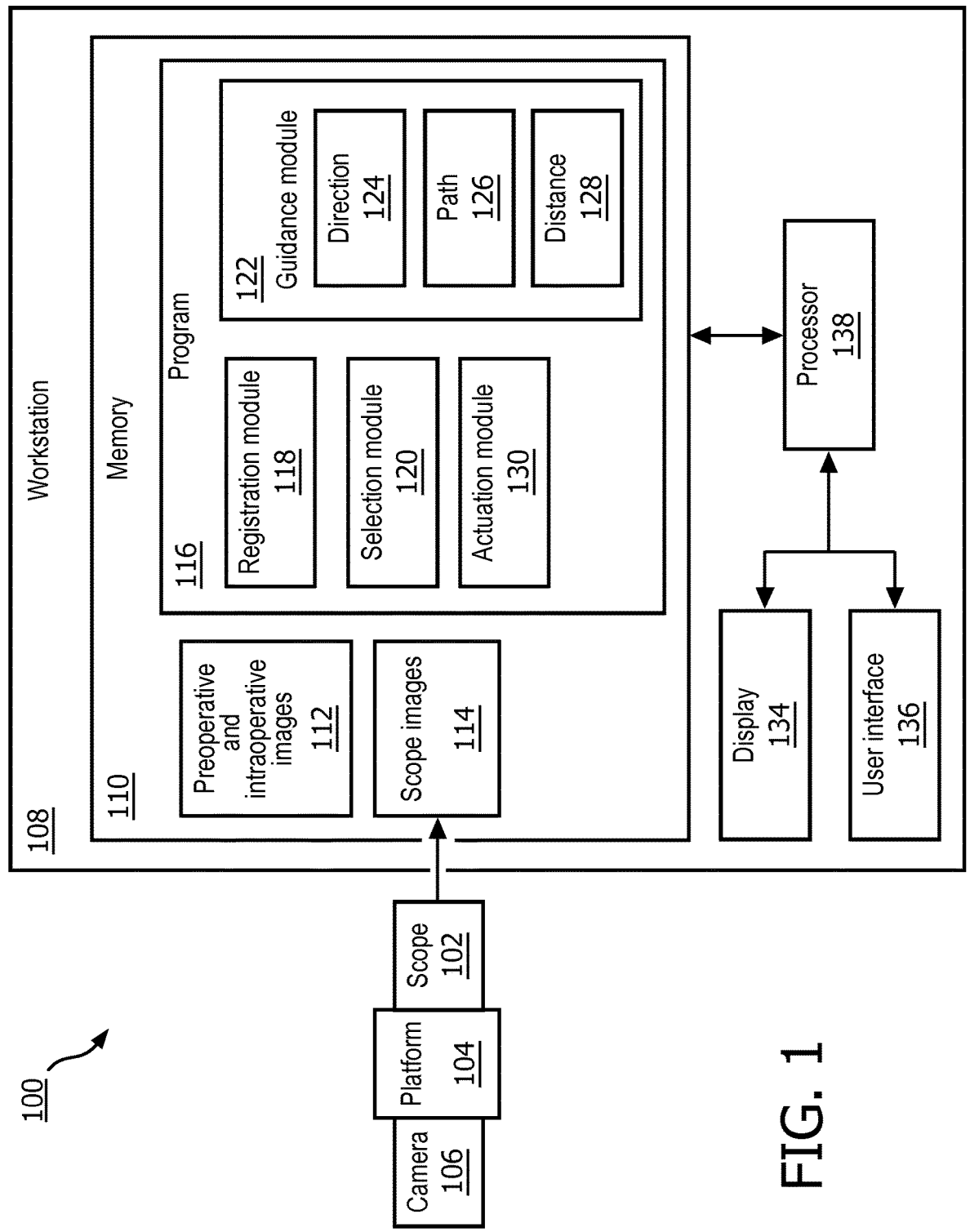
FIG. 1 is a block/flow diagram showing a system for manually steering an endoscope using guidance tools, in accordance with one embodiment.

In accordance with the present principles, embodiments for a system, apparatus and method provide guidance tools for manually steering an endoscope. In one embodiment, preoperative and/or intraoperative images are registered with images of an endoscope. Visual cues may be overlaid onto the endoscope view as guidance tools to permit a user (e.g., surgeon assistant) to steer the endoscope towards selected areas of interest. The motion of the endoscope may be tracked in real-time using image features to update the visual cues. Visual cues may include, but are not limited to: a direction indicator showing the direction to the selected areas of interest, an endoscope tracer showing the motion of the endoscope, a directional error indictor showing the angular error of the motion of the endoscope compared to the direction to the selected areas of interest, a distance error indicator showing distance to the selected areas of interest, and anatomical reference directions showing anatomical directions. Other visual cues are possible and have been contemplated within the scope of the present principles.

In another embodiment, the present principles may preorient an endoscope camera's coordinate system with a user's preferred coordinate system. In order to pre-orient the camera in a preferred direction, the camera of the endoscope may be mounted on an actuated platform. The endoscope user moves the endoscope in the physical direction in which he or she would prefer to correspond to the, e.g., "upwards" direction in the image. The angle between the physical movement of the endoscope and the actual upwards direction in the image is determined and the actuated platform rotates the camera accordingly to pre-orient the coordinate frames. It is noted that the present principles are not limited to the upwards direction, but may include any direction.

It should be understood that the present invention will be described in terms of an endoscope; however, the teachings of the present invention are much broader and are applicable to any optical scope that can be employed in internal viewing of branching, curved, coiled or other shaped systems. In some embodiments, the present principles are employed in tracking or analyzing complex biological or mechanical systems (e.g., digestive systems, circulatory systems, piping systems, passages, mines, caverns, etc.). In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements. Embodiments described herein are preferably displayed for viewing on a display monitor. Such monitors may include any suitable display device including but not limited to handheld displays (e.g., on personal digital assistants, telephone devices, etc.), computer displays, televisions, designated monitors, etc. Depending of the scope, the display may be provided as part of the system or may be a separate unit or device.

It should also be understood that the optical scopes may include a plurality of different devices connected to or associated with the scope. Such devices may include a light, a cutting device, a brush, a vacuum, a camera, etc. These components may be formed integrally with a head on a distal end portion of the scope. The optical scopes may include a camera disposed at a tip of the scope or a camera may be disposed at the end of an optical cable opposite the tip.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Referring now to the drawings in which like numerals represent the same or similar elements and initially to FIG. 1, a system 100 for manually steering an endoscope using guidance tools is illustratively depicted in accordance with one embodiment. System 100 may include a workstation or console 108 from which procedures (e.g., endoscopy) are supervised and managed. Workstation 108 preferably includes one or more processors 138 and memory 110 for storing programs and applications. It should be understood that the functions and components of system 100 may be integrated into one or more workstations or systems.

Memory 110 may store images 112. Images 112 may include preoperative images and intraoperative images, which may be received from systems including, but not limited to, a magnetic resonance imaging (MRI) system, a computed tomography (CT) system, an x-ray system, a 3-D ultrasound system, etc. Memory 110 may also store scope images 114 received from scope 102. In a preferred embodiment, scope 102 is an endoscope to capture intraoperative images of the operation site from camera 106. Scope images 114 may preferably include video from camera 106 of endoscope 102.

The present principles may be applied for different applications of endoscopically-guided minimally invasive surgery. For example, the present principles may be used for cardiac surgery (e.g., minimally invasive coronary artery bypass grafting, atrial septal defect closure, valve repair/replacement, etc.), laparoscopic surgery (e.g., hysterectomy, prostatectomy, gall bladder surgery, etc.), natural orifice transluminal surgery, pulmonary/bronchoscopy surgery, neurosurgical interventions, and videos assisted thoracic surgery. However, it is noted that the teachings of the present principles are much broader than this, as scope 102 may include any type of scope for various types of applications. In one exemplary embodiment, the present principles may be applied to manually navigate a plumber's snake through piping. Other applications are also contemplated.

Workstation 108 may include one or more displays 134 for viewing preoperative and intraoperative images 112 and scope images 114 including guidance features of the present principles. The display 134 may also permit a user to interact with workstation 108 and its components and functions. This is further facilitated by a user interface 136, which may include a keyboard, mouse, joystick, or any other peripheral or control to permit user interaction with workstation 108.

A computer implemented program 116 is stored in memory 110 of workstation 108. The program 116 may include a number of modules, each configured to perform various functions. It should be understood that the modules may be implemented in various combinations of hardware and software.

Program 116 may include registration module 118, which is configured to perform registration between images 112 (e.g., preoperative images and/or intraoperative images) and scope (e.g., endoscope) images 114. Registration is performed as is known in the art.

Program 116 may also include selection module 120, which is configured to allow a user (e.g., a surgeon) to select areas of interest on the preoperative and intraoperative images 112 (e.g., CT or x-ray). For example, a selected area of interest may be a target bypass artery in a coronary artery bypass grafting procedure. Selection module 120 may include the use of display 134 and user interface 136 to facilitate this selection. Selection module 120 then transforms the selected areas of interest from the preoperative and/or intraoperative image coordinate frame to the endoscope coordinate frame using the registration transformation determined in registration module 118.

Program 116 may include guidance module 122, which is configured to use the selected areas of interest in the endoscope view to determine a number of guidance indicators. Guidance module 122 may include, but is not limited to, any or all of direction module 124, path module 126 and distance module 128. Other indicators have also been contemplated.

Figure 2A:
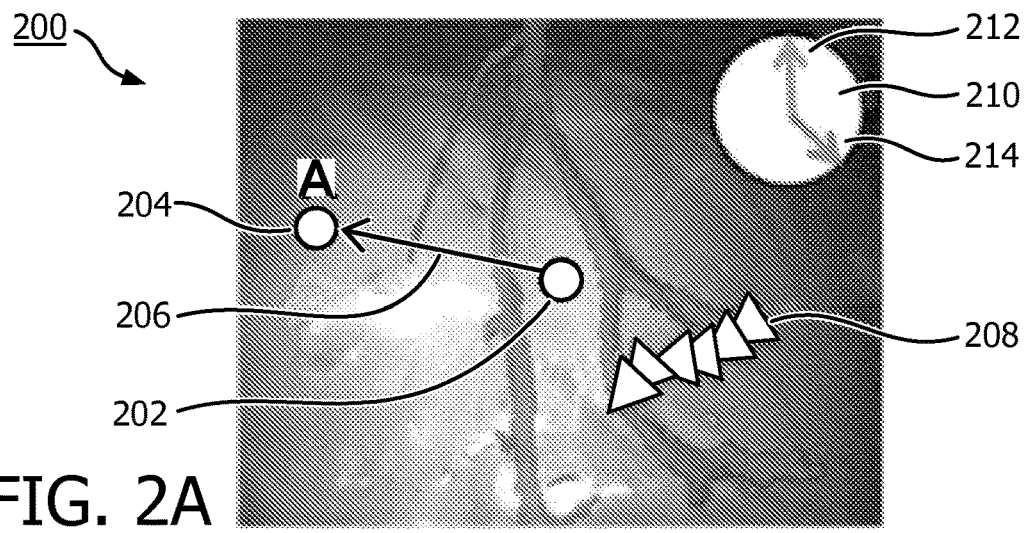
FIG. 2A is an illustrative example of an endoscope image with overlaid direction, path and directional error indicator, in accordance with one embodiment.

Direction module 124 determines a direction from the current center of the endoscope image to the selected areas of interest to overlay a directional indicator onto the endoscope image. Referring for a moment to FIG. 2A, an endoscope image including overlaid indicators 200 is illustratively depicted, in accordance with one embodiment. A directional indicator 206 is overlaid on an endoscope image to show the direction from the center of the endoscope image 202 to the selected areas of interest 204.

Guidance module 122 of FIG. 1 may include path module 126 to further aid the user (e.g., a surgeon or an assistant) in navigating the endoscope. Referring back for a moment to FIG. 2 A, an endoscope trace 208 is overlaid onto an endoscope image to show the motion of the endoscope. The trace 208 is generated by tracking the position of one or more anatomical features that are located at the center of the endoscope image and overlaying an arrow to mark that location on the endoscope image. At each frame or period of frames, the current feature in the center of the image is overlaid with an arrow on the endoscope image, while continuing to track the features previously at the center of the image. Continuing this process, a visual trail may be created to help a user steering an endoscope to navigate to the selected areas of interest 204.

The direction of trace 208 may be compared to the direction of the target area of interest 204 to display an angular error using visual cues. In one embodiment, a dial 210 can be displayed using hands 212 and 214 to indicate the angular offset between the motion of the endoscope 208 and the direction of the selected areas of interest 206, respectively. Other visual cues indicating the angular error are also contemplated. For example, an angle (e.g., in degrees) between direction to selected areas of interest 206 and motion of the endoscope 208 can be displayed.

Figure 2B:
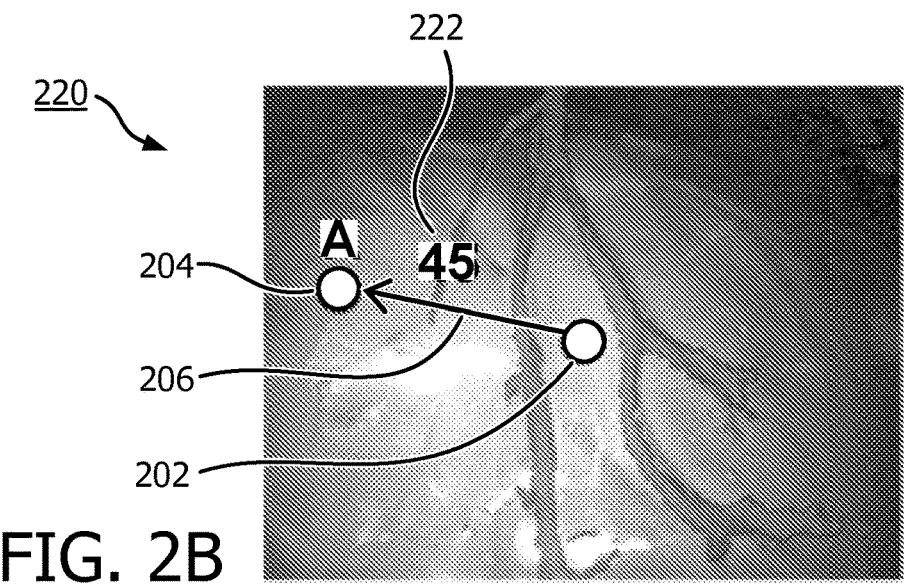
FIG. 2B is an illustrative example of an endoscope image with an overlaid distance error indicator displaying distance, in accordance with one embodiment.
Figure 2C:
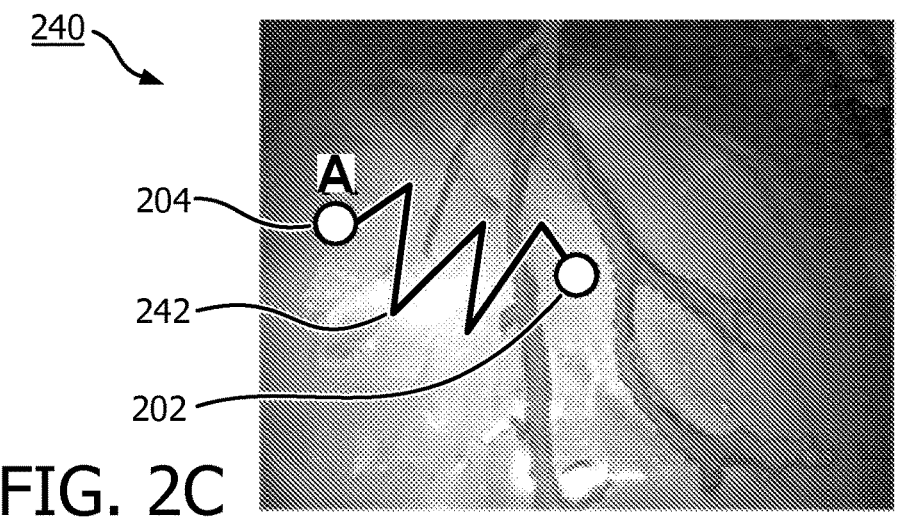
FIG. 2C is an illustrative example of an endoscope image with an overlaid distance error indicator using a virtual spring, in accordance with one embodiment.

Guidance module 122 may also include distance module 128, which is configured to indicate the distance from the center of the endoscope image to the target areas of interest. Referring for a moment to FIG. 2B, an endoscope image with an overlaid distance error indicator 220 is illustratively depicted in accordance with one embodiment. The endoscope image may include directional indicator 206 showing the direction from the center of the endoscope image 202 to target area of interest 204. In one embodiment, a distance 222 (e.g., in pixels) can be indicated as a number on the screen. In another embodiment, a line between the center of the endoscope image 202 and the selected areas of interest 204 can be represented as a function of distance. For example, referring for a moment to FIG. 2C, an endoscope image with an overlaid distance indicator using a virtual spring 240 is illustratively depicted in accordance with one embodiment. A virtual spring 242 joins the center of the endoscope image 202 with the selected areas of interest 204. The virtual spring may appear stretched as the distance between the two points grows further apart and compressed as the distance becomes closer. Other distance error indicators have also been contemplated. For example, the color of the line between the center of the endoscope image 202 and the selected areas of interest 204 can change with distance, with a legend displayed on the screen to define the colors. In another embodiment, the thickness of the line can be modified as distance changes.

In yet another embodiment of the present principles, direction module 124 of FIG. 1 may overlay anatomical reference directions onto the endoscope image. As preoperative and intraoperative images 112 are registered with endoscope images 114 by registration module 118, the anatomical reference directions of the preoperative and intraoperative images are determined. The anatomical reference directions are transformed into the endoscope coordinate system and overlaid onto the endoscope image. Anatomical reference directions may include, but are not limited to, anterior/posterior, left/right and head/foot directions. Other anatomical directions are also contemplated.

Using the overlaid guidance indicators of guidance module 122, a user navigates the endoscope 102. The endoscope motion is traced, as discussed above, to determine if endoscope 102 has reached the selected areas of interest. The operations of the guidance module 122 are repeated until the selected areas of interest are reached. Once the selected area of interest is reached, the process ends.

In one embodiment of the present principles, program 116 of FIG. 1 may also include actuation module 130 to further aid the user in navigating the endoscope 102. Actuation module 130 is configured to pre-orient camera 106 using actuated platform 104 such that a coordinate system of the camera corresponds with a preferred coordinate system of the user. Actuation module 130 receives the direction a user prefers to correspond to the, e.g., upwards direction. For example, a user may physically move the endoscope in the preferred upwards direction. The angle between the physical motion of the endoscope and the true upwards direction of the endoscope image is computed and passed as an input to the actuated platform, which pre-orients the camera accordingly. It is noted that the corresponding direction is not limited to the upwards direction, but rather may include any direction.

Figure 3A:
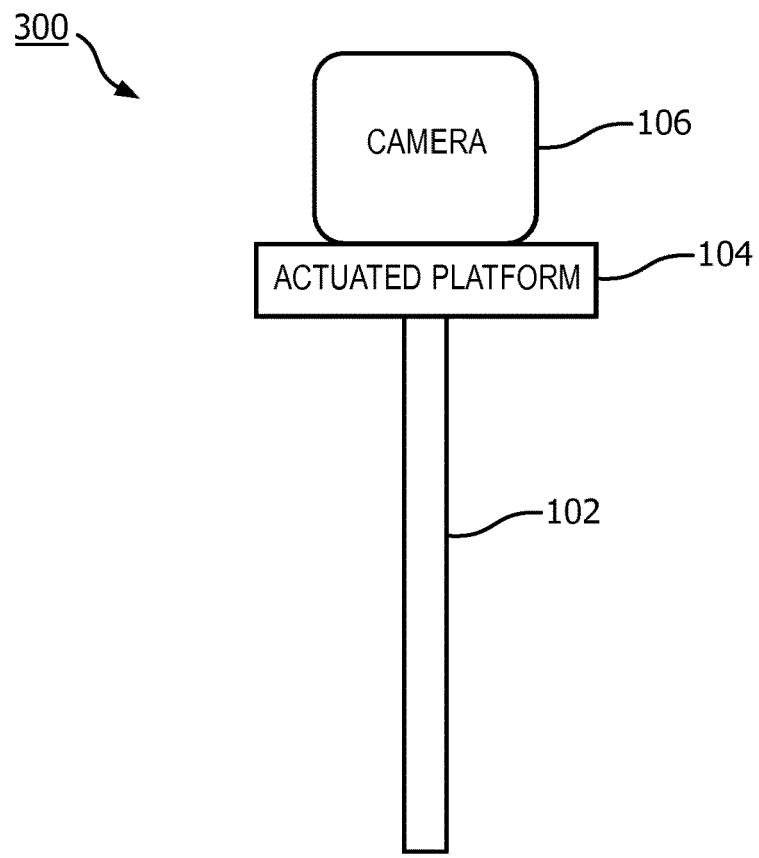
FIG. 3A is a block/flow diagram showing a system for orienting an endoscope camera's coordinate system with an endoscope user's coordinate system, in accordance with one embodiment.
Figure 3B:
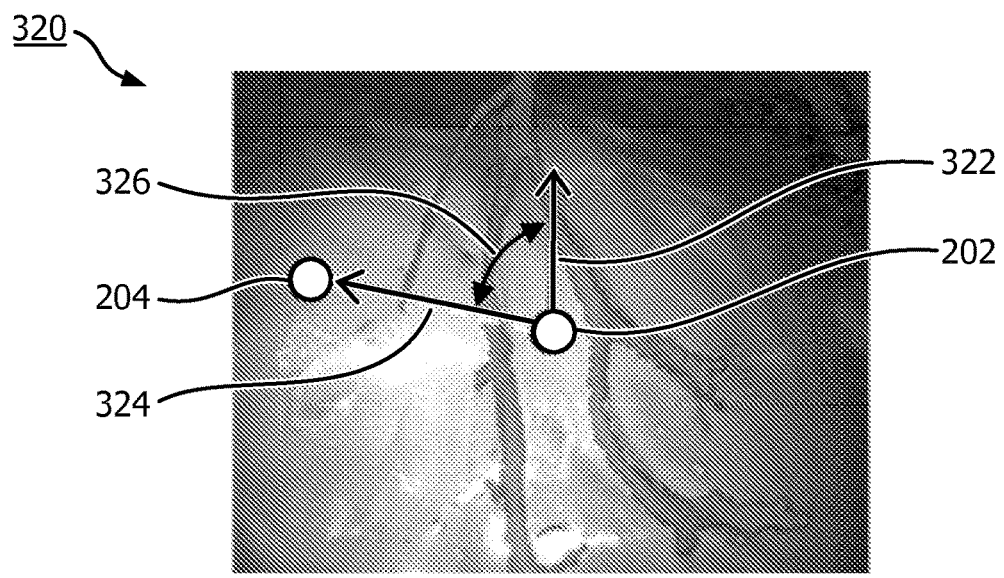
FIG. 3B is an illustrative example of an endoscope image to orient an endoscope camera's coordinate system with an endoscope user's coordinate system, in accordance with one embodiment.

Referring now to FIG. 3A, a system for orienting an endoscope camera's coordinate system with an endoscope user's coordinate system 300 is illustratively depicted in accordance with one embodiment. Camera 106 is mounted on actuated platform 104 on scope 102. Actuated platform 104 rotates according to the received angle to orient the camera accordingly. Referring for a moment for FIG. 3B, an illustrative example of an endoscope image with overlaid orienting indicators 320 is shown in accordance with one embodiment. A user moves the endoscope in a preferred upwards direction, resulting in motion of endoscope 324 from center of image indicator 202. The angle between motion of the endoscope 324 and the true upwards direction of the image 322 is computed to determine angle 326, which is passed to actuated platform 104 to orient the camera accordingly.

Figure 4:
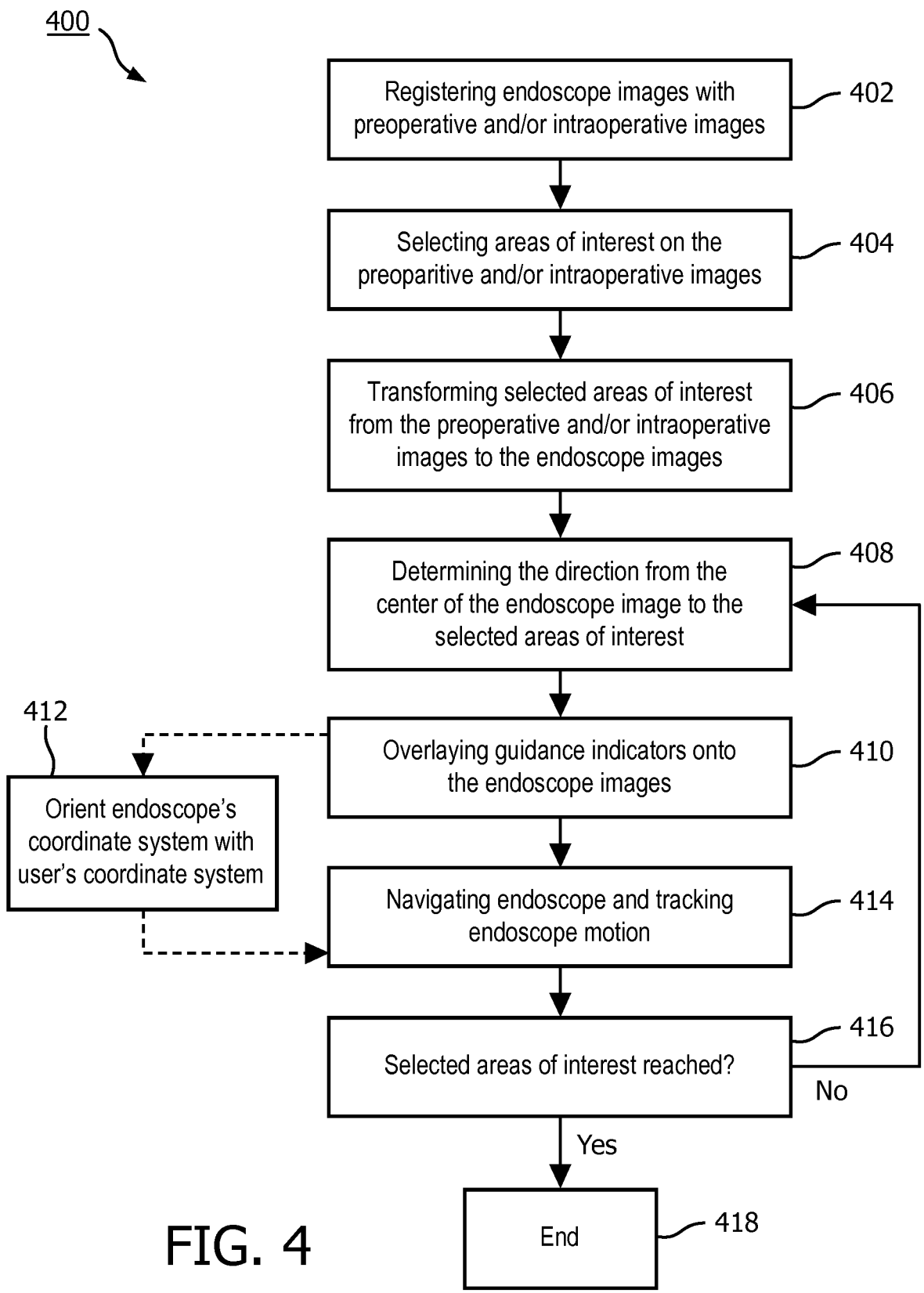
FIG. 4 is a block/flow diagram showing a method for manually steering an endoscope using guidance tools, in accordance with one embodiment.

Referring now to FIG. 4, a method for manually steering an endoscope using guidance tools 400 is illustratively depicted in accordance with one embodiment. In block 402, scope images are registered with preoperative and/or intraoperative images. Scope images are preferably images of an endoscope including a camera to capture intraoperative images of the operation site. Endoscope images may preferably include video. Preoperative and/or intraoperative images may be received from systems including, but not limited to, an MRI system, a CT system, an x-ray system, a 3D ultrasound system, etc. Registration is performed as is known in the art.

In block 404, areas of interest may be selected on the preoperative and intraoperative images. In block 406, the selected areas of interest may be transformed from the preoperative and intraoperative images coordinate frame to the endoscope image coordinate frame. This may include use of the registration transformation determined in block 402.

In block 408, the direction from the current center of the endoscope image to the selected areas of interest is determined in the endoscope image. Using this direction, in block 410, guidance indicators are overlaid onto the endoscope image. Guidance indicators may include, for example, but are not limited to, a directional indicator, an endoscope tracer, a directional error indicator, a distance error indicator, and anatomical reference direction indicator. Other guidance indicators are also contemplated.

In one embodiment, guidance indicators may include a directional indicator overlaid onto the endoscope image to show the direction from the current center of the endoscope image to the selected areas of interest. In another embodiment, an endoscope trace may be overlaid onto the endoscope image showing the endoscope motion. The trace may be generated by tracking the position of each anatomical feature that is located at the center of the endoscope image and overlaying an arrow to mark that location on the endoscope image. At each frame or period of frames, the current feature in the center of the image is overlaid with an arrow on the endoscope image, while continuing to track the features previously at the center of the image. Continuing this process, the positions of each of the features are displayed in the endoscope image to provide a visual trail that can help a user navigate the endoscope.

In yet another embodiment, the endoscope trace may be compared to the direction of the selected areas of interest to determine an angular error, representing the angular offset between the motion of the endoscope and the direction to the selected areas of interest. The angular error may be overlaid onto the endoscope image using visual cues. In an embodiment, a dial including two hands is overlaid onto the endoscope image, where each hand indicates the trace of the endoscope and direction to the selected areas of interest, respectively. In another example, angular error may be indicated by displaying the angle (e.g., in degrees) on the endoscope image.

In one embodiment, guidance indicators may include a distance error indictor overlaid onto the endoscope image. As the endoscope is moved, the distance from the center of the endoscope image to the selected areas of interest will vary. A distance error can be overlaid onto the endoscope images to help the user navigate the endoscope. For example, the distance (e.g., in pixels) can be indicated as a number of the screen. In another example, the line that joins the center of the endoscope image and the selected areas of interest can be represented as a function of distance. This may include representing the line as a virtual spring, which may appear stretched as the distance gets larger and compressed as the distance gets smaller. Alternatively, the color or thickness of the line may change according to distance. Other representations of distance error are also contemplated.

In another embodiment, anatomical reference directions may be overlaid onto the endoscope images. As preoperative and intraoperative images are registered (block 402), the anatomical reference directions of the preoperative and intraoperative images are determined and transformed into the endoscope view. Anatomical reference directions may include, for example, anterior/posterior, left/right and head/foot directions. Other anatomical reference directions are also contemplated.

In block 414, using the guidance indicators overlaid onto the endoscope image, a user can navigate the endoscope with increased efficiency. The endoscope motion is tracked to determine if the selection area of interest is reached. In block 416, if the selected area of interest is not reached, steps 408, 410, 414 and 416 are repeated until the selected area of interest is reached in block 418. Advantageously, the present principles aid a user to navigate an endoscope efficiently, resulting in reduced operating room time.

In one embodiment of the present invention, in block 412, a camera of the endoscope can be pre-oriented such that a coordinate system of the camera corresponds with a preferred coordinate system of the user. A user can indicate a preferred, e.g., upwards direction. This may include a user physically moving the endoscope in the preferred upwards direction. The angle between the physical motion of the endoscope and the actual upwards direction of the endoscope image is computed and passed as an input to an actuated platform mounted between the camera and endoscope. The actuated platform rotates the camera according to the received angle to aid the user in navigating the endoscope. It is noted that the corresponding direction is not limited to the upwards direction, but rather may include any direction.

In interpreting the appended claims, it should be understood that:
   a) the word "comprising" does not exclude the presence of other elements or acts than those listed in a given claim;
   b) the word "a" or "an" preceding an element does not exclude the presence of a plurality of such elements;
   c) any reference signs in the claims do not limit their scope;
   d) several "means" may be represented by the same item or hardware or software implemented structure or function; and
   e) no specific sequence of acts is intended to be required unless specifically indicated.

Having described preferred embodiments for guidance tools to manually steer endoscope using pre-operative and intra-operative 3D images (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for providing navigation guidance for an endoscope, the system comprising:
    at least one processor configured to:
    register a first set of images with a second set of images of the endoscope;
    receive at least one selected area of interest on the first set of images and transform the at least one selected area of interest to an endoscope coordinate frame;
    overlay at least one guidance tool onto a display of the second set of images during the manually guided navigation of the endoscope by a user to the at least one selected area of interest; and
    overlay a path of a current motion of the endoscope onto the display of the second set of images.

2. The system as recited in claim 1, wherein the at least one processor is further configured to:
    orient a camera of the endoscope such that a coordinate system of the camera corresponds with a coordinate system indicated by the user.

3. The system as recited in claim 2, wherein the at least one processor the is further configured to rotate an actuation platform including the camera in accordance with an angle between a direction of a physical movement of the endoscope and a direction within the display of the second set of images of the endoscope.

4. The system as recited in claim 1, wherein the at least one processor is further configured to overlay a direction indicator onto the display of the second set of images, the direction indicator being from a center of a frame of the display of the second set of images to the at least one selected area of interest.

5. The system as recited in claim 4, wherein the at least one processor is further configured to overlay an angular error indicator onto the display of the second set of images to show an angular error between the direction indicator and a path of a motion of the endoscope.

6. The system as recited in claim 1, wherein the overlaid path creates a visual trail of the motion of the endoscope.

7. The system as recited in claim 1, wherein the at least one processor is further configured to:
    generate the path by tracking positions of anatomical features including at least one of anatomical features located at a center of a frame of the display of the second set of images and anatomical features previously located at the center of the frame.

8. The system as recited in claim 1, wherein the at least one processor is further configured to overlay a distance indicator onto the display of the second set of images indicating a distance from a center of a frame of the display of the second set of images to the at least one selected area of interest.

9. The system as recited in claim 8, wherein the distance indicator is a line from the center of the frame to the at least one selected area of interest that varies as a function of distance.

10. The system as recited in claim 9, wherein the line is a virtual spring that appears compressed as the distance decreases and stretched as the distance increases.

11. The system as recited in claim 9, wherein a color of the line varies as a function of distance.

12. The system as recited in claim 1, wherein the at least one processor is further configured to overlay anatomical directions of the first set of images onto the display of the second set of images.

13. A guidance system for providing navigation guidance for an endoscope, the system comprising:
    at least one processor configured to:
    register a first set of images with a second set of images of the endoscope;
    receive at least one selected area of interest on the first set of images and transform the at least one selected area of interest to an endoscope coordinate frame;
    overlay at least one guidance tool onto the second set of images;
    overlay a path of a current motion of the endoscope onto the second set of images; and
    orient a camera of the endoscope such that a coordinate system of the camera corresponds with a coordinate system of a user during manually guided navigation of the endoscope by the user to the at least one selected area of interest.

14. The system as recited in claim 13, wherein the at least one processor is further configured to rotate an actuation platform including the camera in accordance with an angle between a first direction and an actual direction of the first direction.

15. A method for providing navigation guidance for an endoscope, the method comprising:
    registering, by a processor, a first set of images with a second set of images of the endoscope;
    overlying, by the processor, at least one guidance tool onto a display of the second set of images, during a manually guided navigation of the endoscope by a user to at least one selected area of interest, the at least one selected area of interest being selectable on the first set of images and transformable to an endoscope coordinate frame; and
    overlying, by the processor, a path of a current motion of the endoscope onto the display of the second set of images.

16. The method as recited in claim 15, further comprising:
    orienting a camera of the endoscope such that a coordinate system of the camera corresponds with a coordinate system indicated by the user.

17. The method as recited in claim 16, wherein orienting the camera includes rotating an actuation platform including the camera in accordance with an angle between a direction of a physical movement of the endoscope and a direction within the display of the second set of images of the endoscope.

18. The method as recited in claim 15, further comprising:
    overlying a direction indicator onto the second set of images, the direction indicator being from a center of a frame of the display of the second set of images to the at least one selected area of interest.

19. The method as recited in claim 18, further comprising:
    overlying an angular error indicator onto the display of the second set of images to show an angular error between the direction indicator and a path of a motion of the endoscope.

20. The method as recited in claim 15, wherein overlying the path of the current motion of the endoscope onto the display of the second set of images creates a visual trail of the current motion of the endoscope.

21. The method as recited in claim 15, wherein the path is generated by tracking positions of anatomical features including at least one of anatomical features located at a center of a frame of the display of the second set of images and anatomical features previously located at the center of the frame.

22. The method as recited in claim 15, further comprising: overlying a distance indicator onto the display of the second set of images indicating a distance from a center of a frame of the second set of images to the at least one selected area of interest.

23. The method as recited in claim 22, wherein the distance indicator is a line from the center of the frame to the at least one selected area of interest that varies as a function of distance.

24. The method as recited in claim 23, wherein the line is a virtual spring that appears compressed as the distance decreases and stretched as the distance increases.

25. The method as recited in claim 23, wherein a color of the line varies as a function of distance.

26. The method as recited in claim 15, further comprising: overlying anatomical directions of the first set of images onto the display of the second set of images.

\* \* \* \* \*